US008211166B2

(12) United States Patent
Chuter et al.

(10) Patent No.: US 8,211,166 B2
(45) Date of Patent: Jul. 3, 2012

(54) ENDOVASCULAR GRAFTING DEVICE (75) Inventors: Timothy A. M. Chuter, Atherton, CA (US); Matthew J. Fitz, Encinitas, CA (US); Robin W. Eckert, San Jose, CA (US); Juan I. Perez, Sunnyvale, CA (US); Richard Newhauser, Jr., San Francisco, CA (US); Octavian Iancea, Irvine, CA (US); David T. Pollock, San Carlos, CA (US); Arnold M. Escano, Santa Clara, CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 1181 days.

(21) Appl. No.: 10/374,518

(22) Filed: Feb. 26, 2003

(65) Prior Publication Data
US 2003/0199973 A1 Oct. 23, 2003

Related U.S. Application Data (60) Provisional application No. 60/360,323, filed on Feb. 26, 2002.

(51) Int. Cl.
*A61F 2/06* (2006.01)
(52) U.S. Cl. ........................ 623/1.35; 623/1.13; 623/1.16
(58) Field of Classification Search ................ 623/1.13, 623/1.15, 1.35, 1.16, 1.32
See application file for complete search history.

(56) References Cited

U.S. PATENT DOCUMENTS

| 3,657,744 | A |   | 4/1972  | Ersek |           |
|-----------|---|---|---------|-------|-----------|
| 4,140,126 | A |   | 2/1979  | Choudhury | |
| 4,562,596 | A |   | 1/1986  | Kornberg | |
| 4,787,899 | A |   | 11/1988 | Lazarus | |
| 5,064,435 | A |   | 11/1991 | Porter | |
| 5,489,295 | A | * | 2/1996  | Piplani et al. ........... 623/1.35 |
| 5,562,724 | A |   | 10/1996 | Vorwerk et al. | |
| 5,575,817 | A |   | 11/1996 | Martin | |
| 5,609,627 | A |   | 3/1997  | Goicoechea et al. | |
| 5,628,788 | A |   | 5/1997  | Pinchuk | |
| 5,632,772 | A |   | 5/1997  | Alcime et al. | |
| 5,639,278 | A | * | 6/1997  | Dereume et al. ......... 623/1.13 |
| 5,643,339 | A | * | 7/1997  | Kavteladze et al. ...... 623/1.22 |
| 5,653,743 | A |   | 8/1997  | Martin | |
| 5,676,696 | A | * | 10/1997 | Marcade ............... 623/1.35 |
| 5,683,449 | A |   | 11/1997 | Marcade | |
| 5,683,450 | A |   | 11/1997 | Goicoechea et al. | |
| 5,686,451 | A |   | 11/1997 | Kristianson et al. | |

(Continued)

FOREIGN PATENT DOCUMENTS
DE          9319267          4/1994
(Continued)

OTHER PUBLICATIONS

Chuter, et al., "Transfemoral Endovascular Aortic Graft Placement," Journal of Vascular Surgery, vol. 18, No. 2, Aug. 1993, pp. 185-197.

(Continued)

*Primary Examiner* — Corrine M McDermott
*Assistant Examiner* — Melissa Ryckman
(74) *Attorney, Agent, or Firm* — Brooks, Cameron & Huebsch, PLLC (57) ABSTRACT An endovascular grafting device having a main body component and limb components. The device is contemplated to be assembled in-situ for the purpose of treating vascular defects or conditions.

22 Claims, 5 Drawing Sheets

U.S. PATENT DOCUMENTS

| | | | |
|---|---|---|---|
| 5,713,917 A | | 2/1998 | Leonhardt et al. |
| 5,716,365 A | | 2/1998 | Goicoechea et al. |
| 5,718,724 A | | 2/1998 | Goicoechea et al. |
| 5,723,004 A | | 3/1998 | Dereume et al. |
| 5,741,325 A | | 4/1998 | Chaikof et al. |
| 5,755,769 A | | 5/1998 | Richard et al. |
| 5,776,180 A | | 7/1998 | Goicoechea et al. |
| 5,800,508 A | | 9/1998 | Goicoechea et al. |
| 5,824,037 A | | 10/1998 | Fogarty et al. |
| 5,824,042 A | | 10/1998 | Lombardi et al. |
| 5,855,598 A | | 1/1999 | Pinchuk |
| 5,916,263 A | | 6/1999 | Goicoechea et al. |
| 5,938,696 A | | 8/1999 | Goicoechea et al. |
| 5,957,974 A | | 9/1999 | Thompson et al. |
| 5,984,955 A | | 11/1999 | Wisselink |
| 5,993,481 A | * | 11/1999 | Marcade et al. ............. 623/1.35 |
| 6,015,431 A | * | 1/2000 | Thornton et al. ............. 623/1.14 |
| 6,051,020 A | | 4/2000 | Goicoechea et al. |
| 6,099,558 A | | 8/2000 | White et al. |
| 6,102,938 A | * | 8/2000 | Evans et al. .................. 623/1.35 |
| 6,102,940 A | * | 8/2000 | Robichon et al. ............. 623/1.35 |
| 6,117,167 A | * | 9/2000 | Goicoechea et al. ........ 623/1.16 |
| 6,120,522 A | | 9/2000 | Vrba et al. |
| 6,123,722 A | | 9/2000 | Fogarty et al. |
| 6,149,682 A | | 11/2000 | Frid |
| 6,162,246 A | | 12/2000 | Barone |
| 6,165,213 A | | 12/2000 | Goicoechea et al. |
| 6,302,906 B1 | | 10/2001 | Goicoechea et al. |
| 6,319,278 B1 | * | 11/2001 | Quinn .......................... 623/1.13 |
| 6,576,007 B2 | * | 6/2003 | Dehdashtian et al. ........ 623/1.13 |
| 6,576,009 B2 | * | 6/2003 | Ryan et al. .................... 623/1.35 |
| 7,135,037 B1 | * | 11/2006 | Chuter et al. ................... 623/1.1 |
| 2002/0019659 A1 | | 2/2002 | Goicoechea et al. |

FOREIGN PATENT DOCUMENTS

| | | |
|---|---|---|
| FR | 2 678 508 | 1/1993 |
| SU | 660689 | 5/1979 |
| SU | 1217402 | 3/1986 |
| SU | 1457921 | 2/1989 |

OTHER PUBLICATIONS

Parodi, et al. "Transfemoral Intraluminal, Graft Implantation for Abdominal Aortic Aneurysms," Annals of Vacular Surgery, vol. 5, No. 6, 1991, pp. 491-499.

Criado et al., "Transluminal Recanalization, Angioplasty and Stenting in Endovascular Surgery: Techniques and Applications," From Greenhalgh, Vascular and Endovascular Surgical Techniques, $3^{rd}$ Edition, 1994, pp. 49-70.

Marin et al., "Endoluminal Stented Graft Aorto-Bifemoral Reconstruction," from Greenhalgh, Vascular and Endovascular Surgical Techniques, 3.sup.rd Edition, 1994, pp. 100-104.

May et al., "Transluminal Placement of a Prosthetic Graft-Stent Device for Treatment of Subclavian Artery Aneurysm," Journal of Vascular Surgery, vol. 18, No. 6, Dec. 1993, pp. 1056-1059.

Chuter, T., "Bifurcated Endovascular Graft Insertion for Abdominal Aortic Aneurysm," from Greenhalgh, Vascular and Endovascular Surgical Techniques, 3.sup.rd Edition, 1994, pp. 92-99.

Moore, W.S., "Transfemoral Endovascular Repair of Abdominal Aortic Aneurysm Using the Endovascular Graft System Device," from Greenhalgh, Vascular and Endovascular Surgical Techniques, 3.sup.rd Edition, 1994, pp. 78-91.

* cited by examiner

ENDOVASCULAR GRAFTING DEVICE

The present disclosure claims the benefit of U.S. provisional application 60/360,323 filed on Feb. 26, 2002, which is incorporated by reference in its entirety herein.

BACKGROUND OF THE INVENTION

This invention relates to an endovascular graft assembly for treating vasculature of a patient and more specifically to graft system and the attachment of structures thereof.

It is well established that various fluid conducting body or corporeal lumens, such as veins and arteries, may deteriorate or suffer trauma so that repair is necessary. For example, various types of aneurysms or other deteriorative diseases may effect the ability of the lumen to conduct fluids and, in turn, may be life threatening. In some cases, the damage to the lumen is repairable only with the use of prosthesis such as an artificial vessel or graft.

For repair of vital lumens such as the aorta, surgical repair is significantly life threatening or subject to significant morbidity. Surgical techniques known in the art involve major surgery in which a graft resembling the natural vessel is spliced into the diseased or obstructed section of the natural vessel. Known procedures include surgically removing the damaged or diseased portion of the vessel and inserting an artificial or donor graft portion inserted and stitched to the ends of the vessel which were created by the removal of the diseased portion. More recently, devices have been developed for treating diseased vasculature through intraluminal repair. Rather than removing the diseased portion of the vasculature, the art has taught bypassing the diseased portion with a prosthesis and implanting the prosthesis within the vasculature. An intra arterial prosthesis of this type has two components: a flexible conduit, the graft, and the expandable framework, the stent (or stents). Such a prosthesis is called an endovascular graft.

It has been found that many abdominal aortic aneurysms extend to the aortic bifurcation. Accordingly, a majority of cases of endovascular aneurysm repair employ a graft having a bifurcated shape with a trunk portion and two limbs, each limb extending into separate branches of vasculature. Currently available bifurcated endovascular grafts fall into two categories. One category of grafts are those in which a preformed graft is inserted whole into the arterial system and manipulated into position about the area to be treated. This is a unibody graft. The other category of endovascular grafts are those in which a graft is assembled in-situ from two or more endovascular graft components. This latter endovascular graft is referred to as a modular endovascular graft. Because a modular endovascular graft facilitates greater versatility of the matching of individual components to the dimensions of the patient's anatomy, the art has taught the use of modular endovascular grafts in order to minimize difficulties encountered with insertion of the devices into vasculature and sizing to the patient's vasculature.

Although the use of modular endovascular grafts minimize some of the difficulties, there are still drawbacks associated with the current methods. Drawbacks with current methods can be categorized in three ways; drawbacks associated with delivery and deployment of the individual endovascular graft components, drawbacks associated with the main body portion, and drawbacks associated with securing the limb portions to the main body portion.

Moreover, a lack of healthy tissue near the aneurysm being treated provides difficulty with adequately anchoring the main body portion of a modular endovascular graft. If the aneurysm is too close to the renal arteries there may be a lack of healthy tissue to adequately anchor the superior end of the main graft portion without interfering with blood flow in the renal arteries. Anchoring the limb support branches of the main body component in the iliac arteries requires a larger main body component and additional effort and delivery hardware. Allowing the limb support branches of the main body component to float freely in the aneurysm presents additional difficulty with deploying the limb components of the modular endovascular graft within the main body component.

With regard to the main body component of modular endovascular graft, there therefore exists a need for a main body component that facilitates a minimized delivery profile, easier catheterization of the limb support portions and accurate deployment of the limb components, and anchoring of the neck portion near the renal arteries without disrupting cross-blood flow.

The devices of the present invention address these and other needs.

SUMMARY OF THE INVENTION

Briefly and in general terms, the present invention is embodied in an endovascular graft system composed of various components and the attachment of the components to a graft device.

In one aspect, the invention is a main body component of a modular endovascular graft with an attachment frame, for example, a self-expanding attachment structure or stent at its proximal end that is secured to a neck portion of the main body graft. Axial separation of the attachment structure from the main body graft of a modular endovascular graft is contemplated where anchoring the attachment stent above the renal arteries without disturbing cross-blood flow is a concern. If there is sufficient healthy tissue, additional self-expanding structures can be located at the proximal end of the neck portion and a distal end of a limb support portion. Moreover, catheterization of the limb portions of a bifurcated main body component and accurate deployment and attachment of modular limb components can be facilitated by incorporating additional self-expanding attachment or support structures into the main body component. Furthermore, the limb portions may be sutured together from the crotch to the distal end of the shortest limb portion to resist twisting and provide column strength to the main body component during implantation.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

The present invention relates to an endovascular graft and structure and methods for attaching and securing the individual components thereof.

Figure 1:
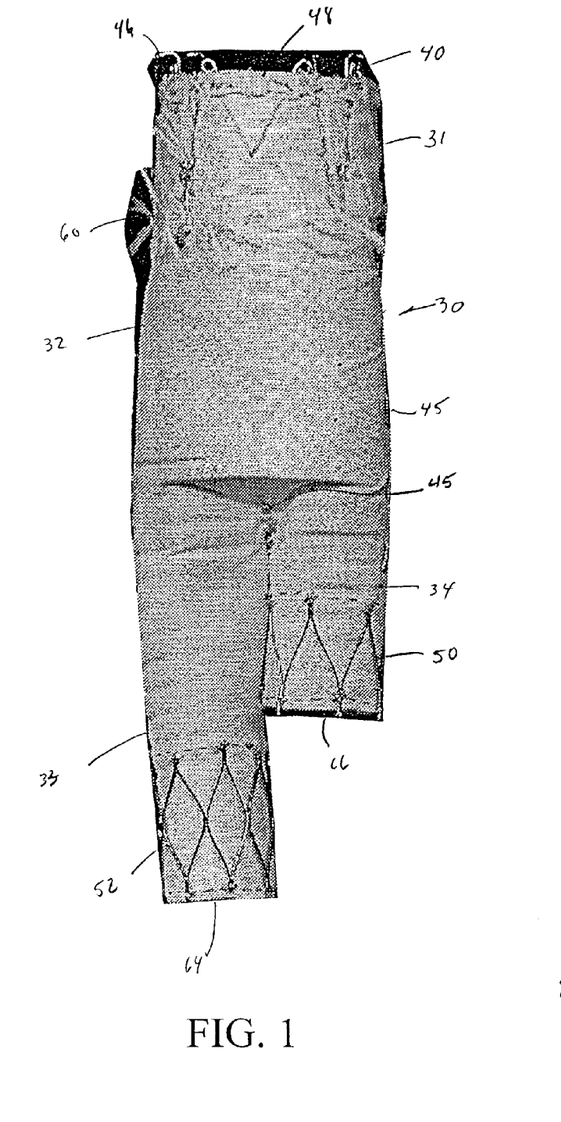
FIG. 1 is a perspective view, depicting a bifurcated endovascular graft main body component of the present invention.

With reference to FIG. 1, there is shown a main body component 30 and attachment stent 40 of a bifurcated endovascular graft that is one aspect of the present invention. The main body component 30 consists of a superior end neck 31, trunk 32 and two limb portions 33, 34. The limb portions 33, 34 facilitate insertion, deployment, and attachment of limb components of the modular endovascular graft. In one aspect of the present invention, one limb portion 34 can be shorter than the other limb portion 33, though the limb portions can have any length as dictated by a particular application. Radiopaque markers 45 placed along the contra-lateral side of the graft material identify the neck 31, mid-point, bifurcation point, and distal end of the contra-lateral limb portion 34, thereby facilitating placement within a patient's body.

The attachment stent 40 can be attached to an inside wall of the main body 30 and includes attachment hooks or barbs 46. The attachment stent is made from wire wound in a generally sinusoidal shape and can have helices at the apices. It is to be borne in mind, however, that the attachment stent 40 can alternatively be placed on an exterior of the main body 30. The attachment stent 40 attachment hooks or barbs 46 facilitate anchoring the stent 40 in a lumen wall and prevent migration of the attachment stent 40 and attached main body component 30. In the embodiment shown in FIG. 1, the hooks 46 extend radially outwardly from a point just beyond a superior end 48 of the main body 30.

The limb portions 33, 34 of the main body 30 can further include stent structures attached to the inside or outside of the limb portions 33, 34. As shown in FIG. 1, the stent structures can have a half-cell configuration 50 or a full-cell configuration 52. The stent structures 50, 52 can be self-expanding or balloon expandable and operate to provide an opening for receiving additional graft components. The stent structures 50, 52 can also be employed to engage vasculature when the device is deployed at a repair site in some patient's anatomy.

The anchoring stent 40 and limb stent structure 50, 52 are sutured to the main body 30 using conventional techniques. The limb portions 33, 34 can also be sewn together to thereby provide a suitable platform for receiving medical devices or additional graft components and create column strength in the main body component during wiring and catheterization of the contra-lateral limb portion for insertion and deployment of the limb component 70. Tufts of yarn 60 are attached to the graft material to aid in securely implanting the main graft 30 within vasculature through the promotion of tissue in-growth.

The main body component 30 can be fully supported along its length or can include stents arranged in a non-overlapping manner. The openings 64, 66 can be equipped with structure configured for mating with separate graft components. The devices can also rely on frictional fits for accomplishing in-situ assembly.

Figure 2:
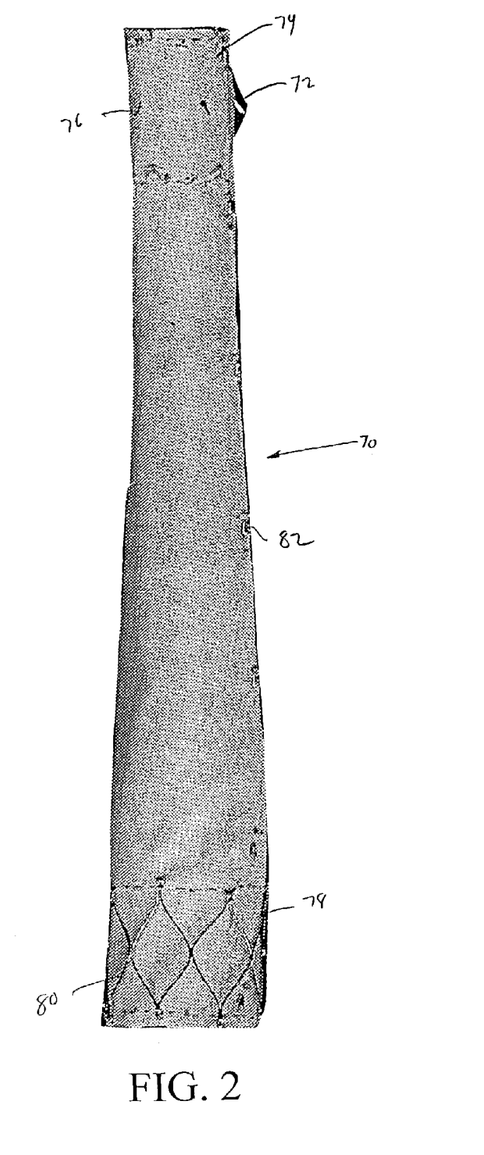
FIG. 2 is a perspective view, depicting a limb component configured for mating with the main body component shown in FIG. 1.

As shown in FIG. 2, a limb component 70 can be equipped with a stent structure 72 positioned interior the limb component 70 at a superior end 74 thereof. The stent structure 72 can be self-expanding or can be balloon expandable and further includes hooks 76 projecting through the graft material of the limb component 70. An inferior end 78 can likewise be equipped with a stent 80 adapted to engage the lumen of the vasculature into which it is placed. The limb component 70 can have a generally tubular, flared or tapered profile and further includes radiopaque markers 82 positioned along its length. Moreover, the limb component 70 can have any suitable length for a particular purpose.

Figure 3:
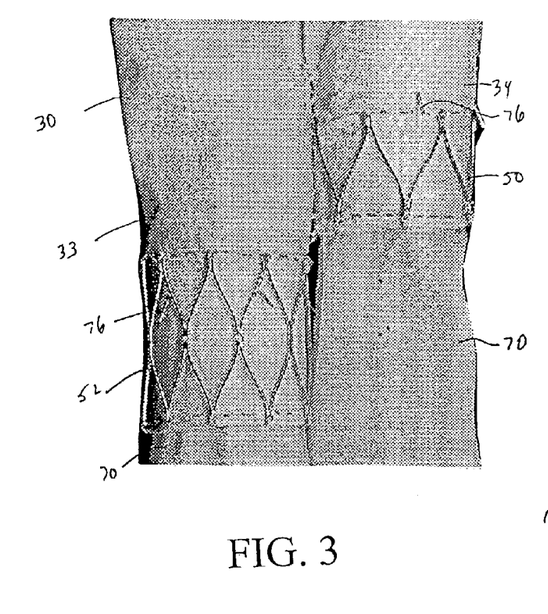
FIG. 3 is a partial perspective and enlarged view, depicting the attachment of limb components in a main body component.

Turning now to FIG. 3, there is shown a main body component 30 having two limb components 70 attached thereto. Once the limb components 70 are placed within the limb portions 33, 34 of the main body component, the hooks or barbs 76 of the stent structure 72 project through the graft material defining the limb portion 33, 34. Moreover, the stent structure themselves securely engage the limbs 33, 34. In this way, the limb portions 70 are fixed to the main body component 30. As shown in the drawings, the hooks 76 can be angled in such a manner to take advantage of blood flow. In FIG. 3, the assembly shown is contemplated to be employed when blood flows in a direction from the main body 30 to the limbs 33, 34.

The endovascular device shown in FIGS. 1-3 embodies a modular design that provides flexibility in sizing to the anatomy of the patient. Additional graft extenders can be employed at both the proximal and distal ends of the assembly. That is, additional limb components 70 can be joined to limb components 70 to further extend the assembly to repair vasculature. For example, in the event it is determined that healthy tissue does not exist at a bifurcation, it may be necessary to place additional limb components 70 within the branch vessel. Similar structure can be employed to extend the main body 30 within the main vessel. As stated, each of these components can be straight, flared or tapered tubular members of increasing or decreasing diameter. It is further contemplated that the grafting system includes various limb sizes, each of which connect to standard sized main body components 30. By employing such a system, lower profile delivery systems can be utilized. For example, a 21.5 fr delivery system (not shown) can be used for a 26 mm implant.

In an alternative embodiment (FIG. 4), the main body component 90 includes an attachment stent 92 particularly configured for transrenal or suprarenal placement. That is, where there is insufficient healthy tissue or where it is otherwise dictated by a patient's anatomy, the main body 30 can employ an attachment stent 92 having hooks or lumen engagement structure 94 which are longitudinally separated from a superior end 96 of the main body 30. In this way, the hooks or barbs 94, for example, can be affixed transrenally or suprarenally while the main body resides inferior the renal arteries. The same approach can be used anywhere in the body where blood through cross-branches in vasculature must be avoided. The attachment stent 92 is made from a tube (such as laser cut) and the hooks or barbs 94 are shape-set to project out from the cylindrical body when the stent is unconstrained by a delivery system. The main body component 90 can be tapered, flared or straight.

Figure 4:
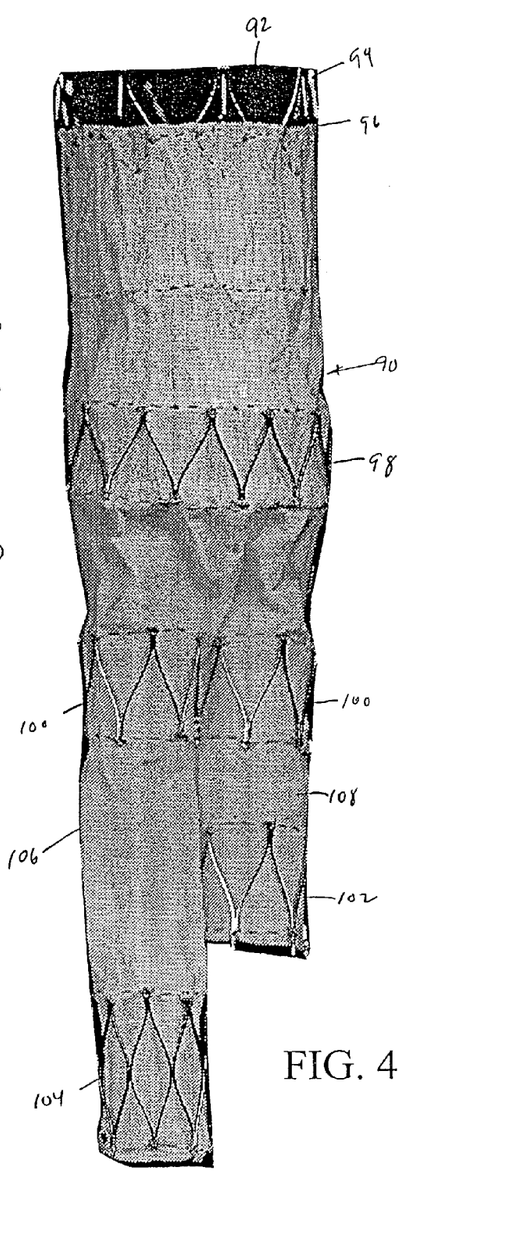
FIG. 4 is a perspective view, depicting an alternative embodiment of a bifurcated stent-graft main body component of the present invention.

The main body component 90 also includes a plurality of supporting structures 98, 100, 102, 104 positioned along its length using conventional techniques. Such structure aids in holding the main body 70 open as well as in some patient's anatomy providing structure for engaging vasculature. As before, limb components can be attached to the main body component 90 as necessary. Also, the limbs 106, 108 can be sewn or otherwise affixed together for providing additional structural support to the device. It is contemplated that such a device can treat aortic necks up to 30 mm via a 20 fr delivery system.

Figure 5:
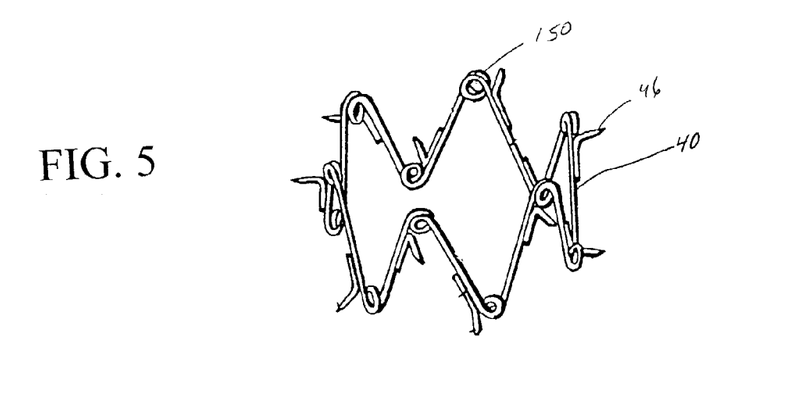
FIG. 5 is a perspective view, depicting an enlarged view of one embodiment of an attachment stent.
Figure 6:
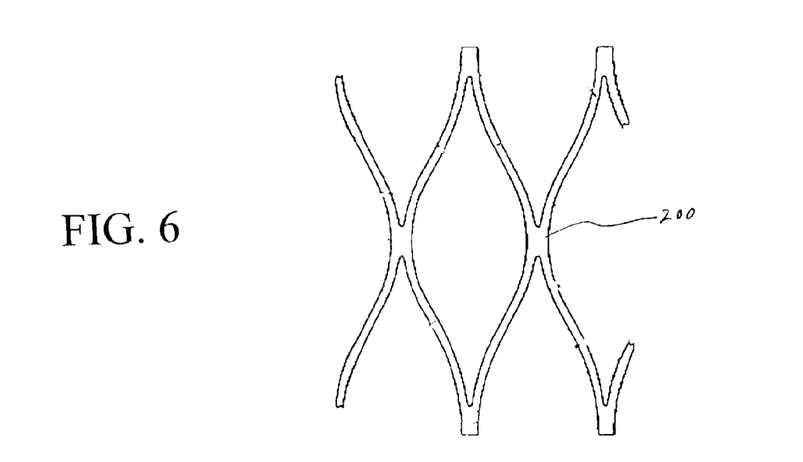
FIG. 6 is a partial perspective view, depicting basic structure for another embodiment of stent structure.
Figure 7:
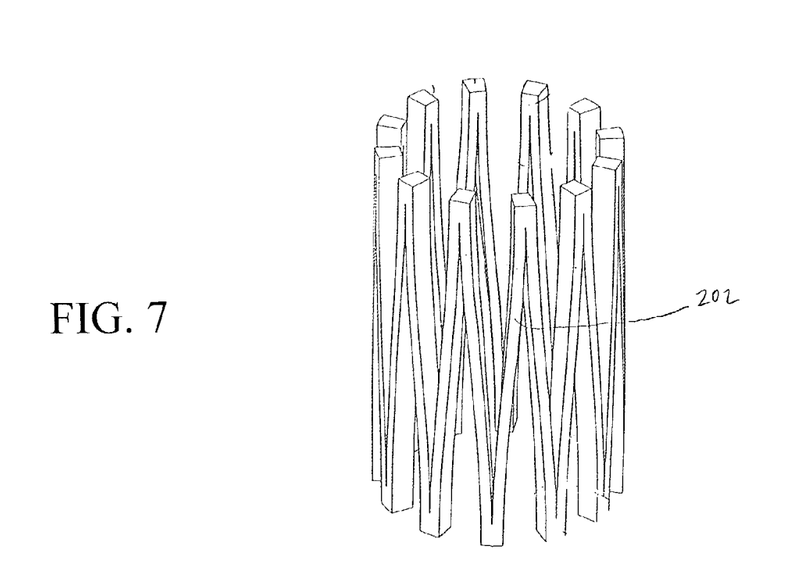
FIG. 7 is a perspective view, depicting basic structure for yet another embodiment of stent structures.
Figure 8:
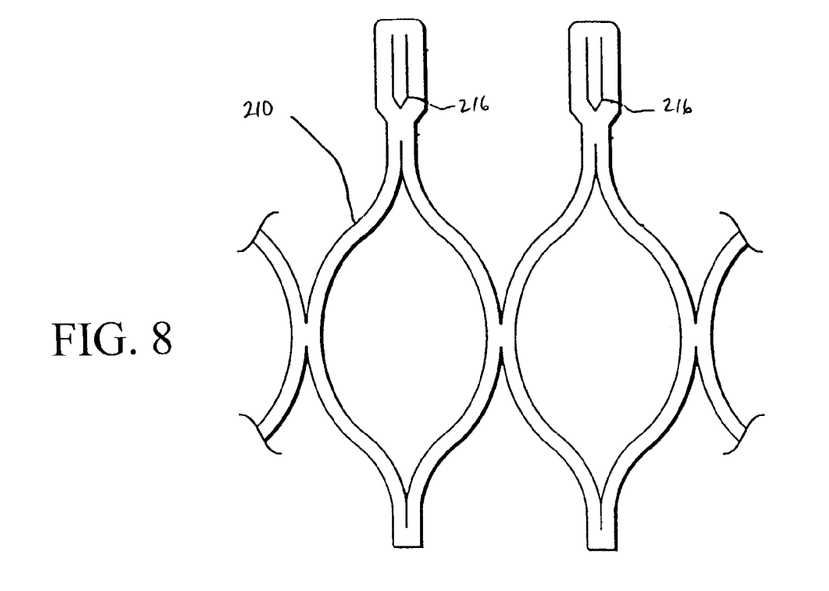
FIG. 8 depicts a stent structure with hooks positioned at apices.
Figure 9:
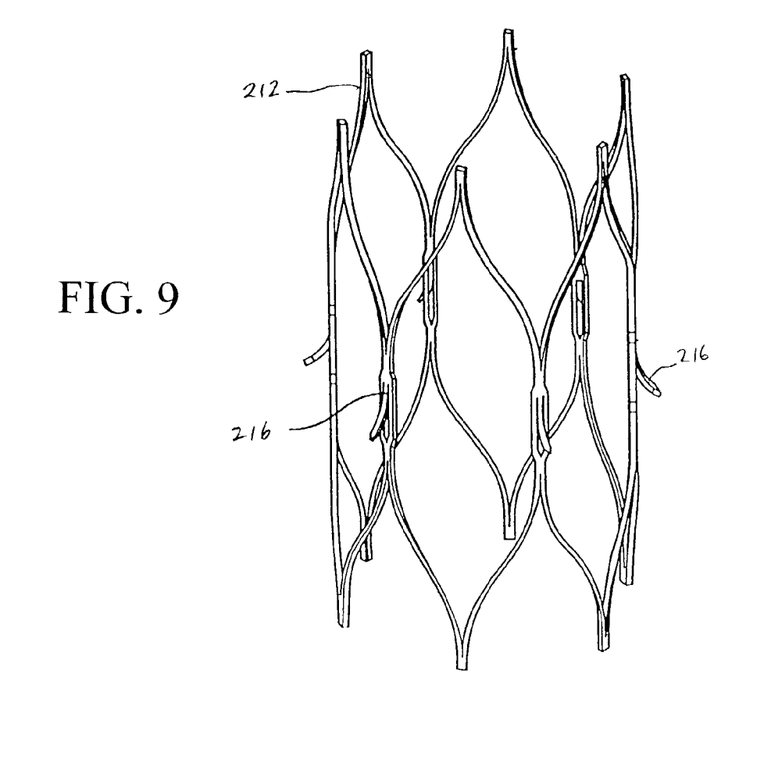
FIG. 9 depicts a stent structure with hooks positioned along a medial portion of the stent.

Enlarged views of the basic structure of the various attachment stents and support structures shown in FIGS. 1-4 are provided for convenience in FIGS. 5-7. In particular, FIG. 5 depicts the basic structure for the attachment stent 40 shown in FIG. 1 and clearly shows helical apices 150. FIGS. 6 and 7 depict basic underlying structure of the full-cell and half-cell stent structures 52, 50 shown in the previous figures. It is to be recognized that the basic underlying structure shown 200, 202 in FIGS. 6 and 7 lack both hooks as well as the looped apices shown in FIG. 1-4 but it is to be recognized that such structures can be added as desired and as previously described. For example, as shown in FIGS. 8 and 9, the stent structures 210, 212 can include hooks 216 configured along a midsection 220 of the stent structure (See also FIG. 2) or at each apex 222 (See also FIG. 4).

Figure 10:
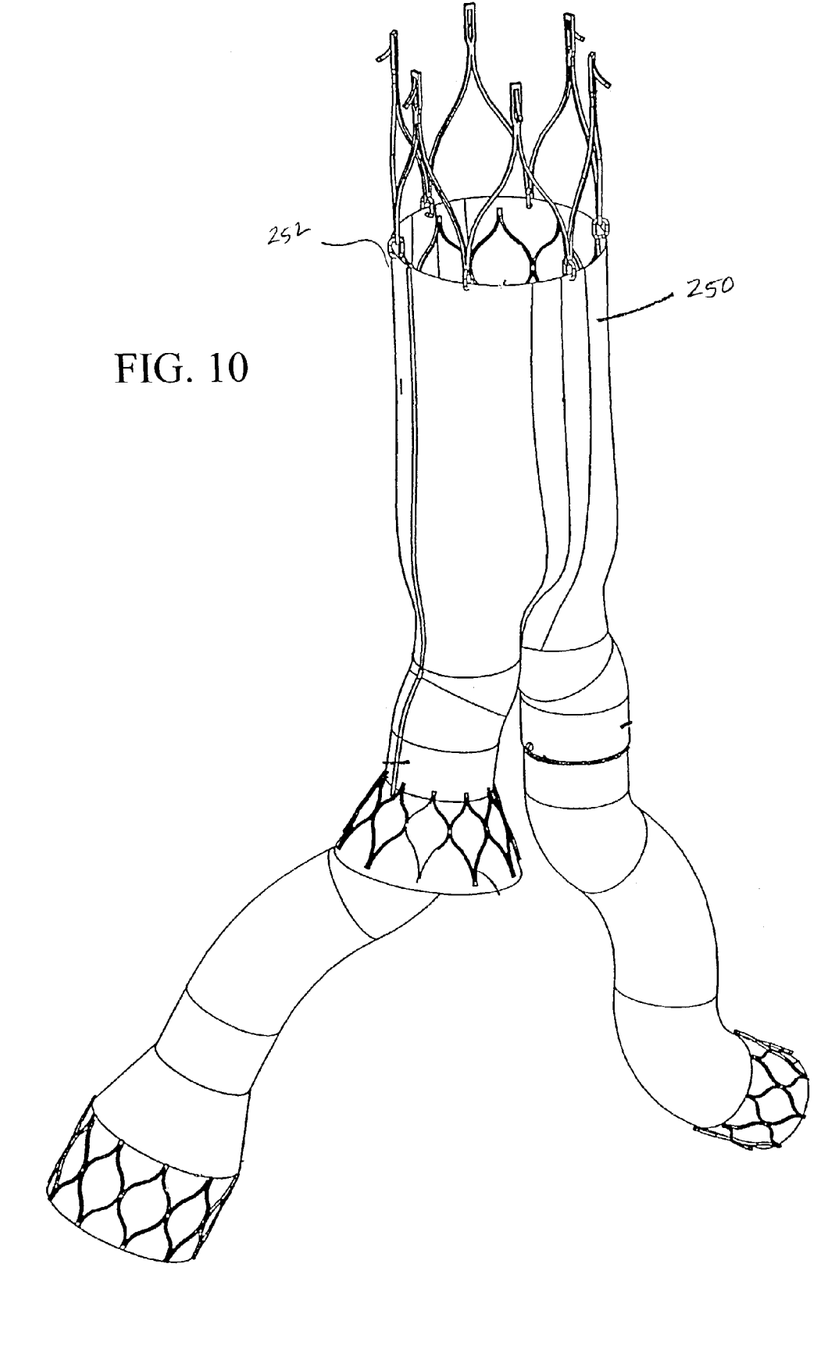
FIG. 10 is a schematic view depicting a modular graft device incorporating straight tubular sections.

Shown in FIG. 10 is a modular graft device 250 incorporating the previously described combination of flared, tapered and straight tubular sections. The assembly depicted in FIG. 10 is merely exemplary in that the present application contemplates a graft with sections that can assume any of the stated configurations. That is, a leg portion can be tapered in one embodiment and flared or a straight tube in another. Likewise, the superior end 252 of the graft device can also embody each of these shapes. Moreover, any of the disclosed stent devices can be positioned along any portion of the inside or outside of the graft devices. Also, as previously described and shown in FIG. 10, a stent device 200 can be placed axially removed from the graft itself to thereby provide anchoring across branch vessels. Although also contemplated, an extender attached to a superior end of the graft device 250 is not shown.

Thus, it will be apparent from the foregoing that, while particular forms of the invention have been illustrated and described, various modifications can be made without the parting from the spirit and scope of the invention. For example, the main body and limb components can each be generally tubular, flared, bifurcated or trifurcated. Also, the stents and other supporting structures can be placed either interior or exterior a particular graft component. Accordingly, it is not intended that the invention be limited, except as by the appended claims.

What is claimed:

1. A modular grafting device, comprising:
  a bifurcated main body formed at least partially by a graft material, the main body including:
    a trunk extending to a bifurcation point;
    a first leg extending distally from the trunk;
    a second leg extending distally from the trunk, the first leg being longer than the second leg, the second leg being sewn together to the first leg along a portion of a length of the second leg;
  a plurality of stents attached to the main body, the plurality of stents including a stent disposed wholly around an outer perimeter of the second leg; and
  at least one leg extender adapted to be placed within the second leg and extending distally away from the main body, the at least one leg extender including an extender stent with barbs, wherein the barbs extend radially outward from the extender stent and through the graft material.

2. The device of claim 1, wherein at least one of the plurality of stents include a closed-cell configuration.

3. The device of claim 1, wherein at least one of the plurality of stents includes a half-cell configuration.

4. The device of claim 1, wherein at least one of the plurality of stents include helical apices.

5. The device of claim 1, wherein the main body further includes a radiopaque marker at the bifurcation point.

6. The device of claim 1, wherein the barbs of the extender stent are adapted to extend through a wall defining the main body.

7. The device of claim 1, wherein the extender is tapered.

8. The device of claim 1, wherein the barbs of the extender stent extend through a wall defining the extender.

9. The device of claim 1, wherein selected struts of the plurality of stents are configured on an outside surface of the main body.

10. The device of claim 1, wherein the first leg is contemplated to extend to a branch vessel when placed within vasculature.

11. The device of claim 1, wherein one of the plurality of stents is configured about both the first and second legs.

12. The device of claim 1, wherein the first and second legs are attached along an entire length of the second leg.

13. The device of claim 1, wherein certain of the plurality of stents include a plurality of apices and closed-looped portions formed at one or more of the apices.

14. The device of claim 1, wherein certain of the plurality of stents include apices and further comprise hooks extending from the apices.

15. The device of claim 1, wherein certain of the plurality of stents include hooks formed along a midsection thereof.

16. The device of claim 1, wherein the plurality of stents are self-expanding.

17. The device of claim 1, further comprising a superior stent connected to, but longitudinally separated from, the main body.

18. The modular grafting device according to claim 1, wherein each of the plurality of stents have a different radial dimension or are each individually defined by struts having unique lengths or curvatures, the main body further comprising main body radiopaque markers forming a dashed line and extending along only one of the first and second legs and the extender includes extender radiopaque markers forming a dashed line extending along a length of the extender.

19. The modular grafting device according to claim 1, wherein at least one of the first and second legs has an outwardly extending flared end.

20. A modular grafting device, comprising:
  a bifurcated main body having a graft material covering at least a portion of the main body, the main body including:
    a trunk extending to a bifurcation point;
    a first leg extending distally from the trunk;
    a second leg extending distally from the trunk, the first leg being longer than the second leg, the second leg being sewn together to the first leg along a portion of a length of the second leg;
  a plurality of separate stents coupled to the graft material, the plurality of separate stents arranged in a non-overlapping manner, the plurality of stents including a stent disposed wholly around an outer perimeter of the second leg; and
  at least one leg extender adapted to be placed within the second leg and including an extender stent with hooks, wherein the hooks extend radially outward through the graft material.

21. The modular grafting device according to claim 20, wherein the plurality of separate stents comprise a first stent coupled to the trunk, a second stent coupled to the first leg and a third stent coupled to the second leg.

22. A modular grafting device, comprising:
- a bifurcated main body having a graft material forming at least a portion of the main body, the main body including:
  - a trunk extending to a bifurcation point;
  - a first leg extending distally from the trunk;
  - a second leg extending distally from the trunk, the first leg being longer than the second leg, the second leg being sewn together to the first leg along a portion of a length of the second leg, the second leg having a stent circumscribing an outer perimeter of the second leg; and
- at least one leg extender adapted to be placed within the second leg and extending distally away from the main body.

* * * * *